United States Patent [19]

Waterstrat

[11] 4,018,600

[45] Apr. 19, 1977

[54] METHOD FOR ELIMINATING GAMMA$_2$ PHASE FROM DENTAL AMALGAM AND IMPROVED DENTAL AMALGAM COMPOSITION

[75] Inventor: Richard M. Waterstrat, Gaithersburg, Md.

[73] Assignee: American Dental Association Health Foundation, Chicago, Ill.

[22] Filed: Sept. 29, 1975

[21] Appl. No.: 617,594

[52] U.S. Cl. .............................. 75/169; 75/173 R
[51] Int. Cl.$^2$ .................... C22C 5/06; C22C 7/00
[58] Field of Search ...................... 75/173 R, 169

[56] References Cited

UNITED STATES PATENTS 3,762,917  10/1973  Johnson ............................ 75/169

FOREIGN PATENTS OR APPLICATIONS 45-8552  3/1970  Japan ............................... 75/173 R

*Primary Examiner*—L. Dewayne Rutledge
*Assistant Examiner*—E. L. Weise
*Attorney, Agent, or Firm*—Allegretti, Newitt, Witcoff & McAndrews

[57] ABSTRACT

An improved alloy for a dental amalgam includes silver and tin and the additional element, manganese. The alloy is comprised of a minimum of about 60% by weight silver, a maximum of about 15% by weight manganese and the balance tin. Various amounts of other constituents known to those in the art such as gold, copper, zinc and mercury may be included.

5 Claims, No Drawings

METHOD FOR ELIMINATING GAMMA$_2$ PHASE FROM DENTAL AMALGAM AND IMPROVED DENTAL AMALGAM COMPOSITION

The invention described herein was made in the course of work under a grant or award from the Department of Health, Education and Welfare.

BACKGROUND OF THE INVENTION

This invention relates to an alloy for a dental amalgam and, more particularly, to a new class of such alloys which include silver, tin and manganese.

Amalgams are presently the principal material used by dentists for restoration of decayed teeth. About 75% of dental restorations are by amalgams. Amalgams are plastic at normal room and body temperature for a few minutes before they harden. Little or no change in volume occurs as a result of becoming hard. Amalgams combine the characteristics of high compressive and moderate tensile strength with the ability to withstand the corrosive environment defined by the mouth. Additionally, they are substantially non-toxic.

Generally, the alloy from which amalgams are made includes a mixture of silver and tin. The American Dental Association has established various standards for such alloys. Following is the American Dental Association specification for compositions of alloys used in making amalgams:

| Silver | Tin | Copper | Zinc | Mercury |
| --- | --- | --- | --- | --- |
| Min wt % | Max wt % | Max wt % | Max wt % | Max wt % |
| 65 | 29 | 6 | 2 | 3 |

The above composition standard was adopted by the American Dental Association effective June 1, 1970 and is also identified as American National Standard No. Z156.1–1970. Incorporated herewith by reference is the publication entitled "Guide to Dental Materials and Devices," Seventh Edition 1974–1975, copyright 1974, American Dental Association. Particular attention is directed to chapter 3 of this reference entitled "Amalgam and Mercury" as well as Specification No. 1 of the A.D.A. specifications for dental materials.

Amalgam alloys complying with present specifications and standards are generally silver-tin alloys containing approximately three parts of silver and one part of tin. This alloy is often referred to as the gamma phase ($\gamma$) or Ag$_3$Sn. In practice, the powdered alloy and mercury are subjected to trituration, thereby facilitating a reaction between mercury and the alloy. The mercury combines with the alloy to form new solid phases from the pulverized or triturated amalgam.

The chemical reaction during amalgamation may be described as follows:

$$Ag_3Sn + Hg \rightarrow Ag_2Hg_3 + Sn_7Hg$$

Thus, in addition to a gamma$_1$ phase ($\gamma$) (Ag$_2$Hg$_3$), a tin-mercury phase, often referred to as the gamma$_2$ phase ($\gamma_2$), is formed. The gamma$_2$ phase has a simple hexagonal crystal structure and may contain 5 to 12% atomic percent mercury. The designation for this phase is uncertain; though, the phase is often designated as Sn$_7$Hg or Sn$_8$Hg.

The tin-mercury phase in a dental amalgam is known as a weak constituent relative to the silver-tin and silver-mercury phases. Nonetheless, the gamma$_2$ phase may comprise up to 10% of the amalgam. The gamma$_2$ phase has been associated with poor corrosion resistance and excessive flow or creep under an applied stress. To overcome the deficiencies noted in the gamma$_2$ phase, the subject matter of the present invention has been developed.

SUMMARY OF THE INVENTION

Briefly, the invention comprises an improved alloy for amalgams wherein manganese is used in silver-tin based dental alloys to react with the tin during amalgamation and thus reduce or eliminate the tendency of these alloys to form the undesirable gamma$_2$ phase.

Thus, it is an object of the present invention to provide an improved alloy for dental amalgams.

It is a further object of the present invention to provide an improved alloy for dental amalgams utilizing manganese in order to improve corrosion resistance and reduce excessive flow or creep.

Still another object of the present invention is to provide an improved alloy for dental amalgams which is inexpensive and effective with an ability to perform acceptably and meet standard specifications.

These and other objects, advantages and features will be set forth in the detailed description which follows.

DESCRIPTION OF THE PREFERRED EMBODIMENT

The alloy of the present invention utilizes manganese in combination with a silver-tin dental alloy. The manganese reacts with the tin during the amalgamation process, thus reducing or eliminating the tendency of such alloys to form the undesirable gamma$_2$ phase during amalgamation.

As an example of the particular class of compounds which result during the amalgamation of the alloy, the following formulation is set forth:

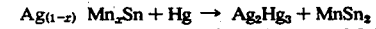

$$Ag_{(1-x)} Mn_x Sn + Hg \rightarrow Ag_2Hg_3 + MnSn_2$$

The relative amounts of Ag$_2$Hg$_3$ and MnSn$_2$ which are formed depend upon the amount of manganese. If no manganese is present, then the reaction which occurs is the standard amalgam reaction recited above in the Background of the Invention. Increased amounts of manganese will decrease progressively the amount of tin which is available to form the gamma$_2$ phase.

Typically, in such alloys, an amount of the original alloy particles (Ag$_3$Sn) remains unreacted. Thus, one normally obtains a solid mixture of the products of the reaction together with residual, unreacted alloy particles. A certain amount of manganese remains in the unreacted portion and thus available for reaction with tin. It is therefore difficult to predict exactly how much manganese is needed to prevent the formation of the gamma$_2$ phase. A lower limit of the amount, however, can be calculated by assuming that all the manganese is available for reaction. On this base, it is estimated that about 8% manganese should suffice to eliminate all the gamma$_2$ phase; however, experience indicates that manganese in an amount of 2% by weight to a maximum of 15% by weight is efficacious in the practice of the invention.

Additions of manganese in excess of the amount required to eliminate the gamma$_2$ phase may provide beneficial effects. Alloys have been tested containing 12% manganese. Such alloys possessed excellent resistance to creep or flow as compared with an 8% manganese alloy of the present invention or with other commercial amalgam alloys. Tests also indicate that amalgams prepared from the above-described alloys are equally as corrosion resistant as other commercial alloys. Following are examples of alloys and specific tests performed:

EXAMPLE NO. 1

Homogeneous mixture comprising 62% silver, 12% manganese and 26% tin was prepared by atomization of the molten metal alloy. This resulted in the formation of approximately spherical particles having a particle size between 325 and 400 mesh. An amalgam was prepared from the alloy using a 6.2:6 ratio of mercury to alloy. The amalgam was prepared in a commercial amalgamator in accordance with conventional procedures. All tests were conducted using methods described in the American Dental Association specification No. 1 referenced above. Corrosion resistance was determined to be as good as any of the prior art amalgams. Resistance to creep or flow was improved relative to prior art amalgams. Typical comparative data is set forth below with the amalgam of the 12% alloy of the present invention listed first:

| Alloy | ADA Flow Test[1] | Dimensional Change | 24 hr. Diam.[3] Tensile Strength |
|---|---|---|---|
| 12% Mn alloy | 0.16 to 0.03% | 0 to +4 | 5700 to 7500 psi |
| Dispersalloy[4] | 0.6% | +13 | 7300 psi |
| 10% Au alloy | | +20 | 7750 to 8900 psi |
| Optalloy[5] | 1.09% | −7 | 10,700 to 11,100 psi |
| Velvalloy[6] | 0.81% | −12 | |
| Spheralloy[7] | 0.86% | −17 | |

| Alloy | 15 min. Diam.[2] Tensile Strength |
|---|---|
| 12% Mn alloy | 1760–1970 psi |
| Dispersalloy | 300 psi |
| Optalloy | 800 psi |
| Velvalloy | 550 psi |
| Spheralloy | 650 psi |

This amalgam was sectioned, polished and submitted to examination by X-ray area scanning in an electron microprobe. The characteristic X-ray emission from tin, manganese and silver was mapped separately on the same area of the sample at a magnification of about 1000X. This technique revealed that each residual spherical particle of the gamma$_1$ phase was surrounded by a layer of manganese-tin compound. There was no evidence of any tin-mercury compound. X-ray diffraction patterns of this amalgam were difficult to interpret due to line overlaps but the strong-intensity line of the gamma phase, usually present in patterns from conventional amalgams, was in this case replaced by a weak-intensity line.

1. American Dental Association Specification No. 1 flow test.
2. American Dental Association Specification No. 1 tensile strength.
3. The same test as defined by No. 2, except after 24 hours.
4. Trade name for amalgam alloy sold by American Silver & Mercury Producers.
5. Trade name for amalgam alloy sold by L. D. Caulk Co., Division of Dentsply International, Inc.
6. Trade name for amalgam alloy sold by S. S. White Division, Pennwalt Corp.
7. Trade name for amalgam alloy sold by Ken Mfg. Co.

EXAMPLE NO. 2

The same experiment was performed using an alloy including 66% silver, 8% manganese and 26% tin. Substantially identical results were observed.

It is clear that changes to the composition may be effected and still remain within the scope of the invention. Thus, the amalgamation procedure may call for additional mercury. Other alloying agents such as copper, zinc or mercury may be included in the alloy. The invention therefore is to be limited only by the following claims and their equivalents.

What is claimed is:
1. An improved alloy for dental amalgam consisting essentially of about 62% by weight silver, about 12% by weight manganese and the balance tin.
2. An improved alloy for dental amalgam consisting essentially of about 66% by weight silver, about 8% by weight manganese and the balance tin.
3. A dental amalgam consisting essentially of an alloy including a minimum of 60% by weight silver and about 2% to a maximum of 15% by weight manganese and the balance tin; in combination with mercury.
4. An improved method for making a dental amalgam comprising the steps of mixing mercury with an alloy, said alloy consisting essentially of a minimum of 60% by weight silver, about 2% to a maximum of 15% by weight manganese and the balance tin.
5. The improved method of claim 4 wherein the weight ratio of said mercury to said alloy is about 1:1 or greater than 1:1.

* * * * *